United States Patent [19]

Winkler

[11] Patent Number: 5,619,475
[45] Date of Patent: Apr. 8, 1997

[54] METHOD OF PREDICTING MECHANICAL FAILURE IN FORMATION UTILIZING STRESS DERIVATIVES WHICH MEASURE FORMATION NONLINEARITY

[75] Inventor: Kenneth W. Winkler, Ridgefield, Conn.

[73] Assignee: Schlumberger Technology Corportion, New York, N.Y.

[21] Appl. No.: 555,796

[22] Filed: Nov. 9, 1995

Related U.S. Application Data

[63] Continuation of Ser. No. 298,718, Aug. 31, 1994, abandoned, which is a continuation-in-part of Ser. No. 220,717, Mar. 30, 1994, Pat. No. 5,544,127.

[51] Int. Cl.$^6$ ............................................. G01V 1/40
[52] U.S. Cl. ........................... 367/27; 181/105; 367/35; 367/86
[58] Field of Search .............................. 367/27, 35, 86; 181/102, 103, 105; 175/50

[56] References Cited

U.S. PATENT DOCUMENTS

| H1,156 | 3/1993 | Siegfried | 367/31 |
|---|---|---|---|
| 4,052,889 | 10/1977 | Mucciardi et al. | 73/67.8 |
| 4,399,525 | 8/1983 | Thompsen et al. | 367/73 |
| 4,951,264 | 8/1990 | Yamamoto | 367/15 |
| 5,353,637 | 10/1994 | Plumb et al. | 73/151 |

OTHER PUBLICATIONS

Sergio Kostek, PHD Thesis, MIT, Apr. 1993, "Linear and Nonlinear Electric Wave Propagation in a Fluid Filled Borehole"; pp. 1–187.
Miles et al, Petroleum Technology, Nov. 1948, pp. 186–191.
Nikolaev, A. R.; IA SPIE I Nonlinear Seismal. Int. Symp (Suzdal USSR Oct. 31, 1986), Phys.
Earth Planetary Inferiors, Sal. 50,#1, pp. 1–7, Jan. 1988; abstract only provided herewith.
Hughes et al, Physical Review, vol. 92,#5, Dec. 1, 1953, pp. 1145–1149.

Velocity–Porosity–Clay Content Systematics of Poorly Consolidated Sandstones by Kowallis et al., Jour. of Geophysical Research, vol., 89, No. B12, pp. 10,355–10,364, Nov. 10, 1984.
Effects of porosity and clay content on wave velocities in sandstones, by Han et al., Geophysics, vol. 51 No. 11, Nov. 1986 pp. 2093–2107.
Relationship between compressional–wave and shear–wave velocities in clastic silicate rocks by Castagna et al. Geophysics, vol. 50, No. 4, Apr. 1985 pp. 571–581.
Acoustic Character Logs and Their Applications in Formation Evaluation by Pickett, Jour. of petroleum Technology vol. 15, pp. 659–667 (1963).

(List continued on next page.)

Primary Examiner—Nelson Moskowitz
Attorney, Agent, or Firm—David P. Gordon; Martin D. Hyden; Brigitte L. Jeffery

[57] ABSTRACT

A method for determining whether a formation is subject to incipient failure are disclosed. The method comprises determining in situ a nonlinear parameter of a formation, and determining whether the nonlinear parameter and/or a derivative of that nonlinear parameter as a function of stress has a relatively large negative value in order to determine whether the formation is subject to incipient failure. In a preferred embodiment, the nonlinear parameter of the formation is a derivative of the square of the shear or compressional velocity with respect to formation stress. The nonlinear parameter of the derivative of the square of the shear velocity with respect to stress is considered to have a large negative value when it is $\leq -0.1$ (km/sec)$^2$/MPa, while the nonlinear parameter of the derivative of the square of the compressional velocity with respect to stress is considered to have a large negative value when it is $\leq -0.2$ (km/sec)$^2$/MPa. The derivative of the derivative of the square of the shear or compressional velocity with respect to stress is considered to have a large negative value when the derivative is $\leq -0.06$ (km/sec)$^2$/(MPa)$^2$. Typically, rocks will fail if uniaxially stressed between 11–5 MPa beyond any of those points.

17 Claims, 4 Drawing Sheets

OTHER PUBLICATIONS

Borehole Flexural modes in anisotropic formations, by Sinha et al., Geophysics vol., 59, No. 7, Jul. 1994 pp. 1037–1052

Numverical Computation of individual far-field arrivals excited by an acoustic source in a borehole by Kurkjian, Geophysics vol. 50, No. 5, May 1985, pp. 852–866.

Third-order elastic constants for an inviscid fluid, by Kostek et al., Jour. Acoust. Soc. Am. 94(5) Nov. 1993 pp. 3014–3017.

Third-order Elastic Constants and the Velocity of Small Amplitude Elastic Waves in Homogeneously Stressed Media by Thurston et al. Physical Review, vol. 133, No. 6A Mar. 1964, pp. A1604–1610.

Sound Waves in Deformed Perfectly Elastic Materials, Acoustoelastic Effect by Toupin et al., Jour. of Acoustical Society of America, vol. 33, No. 2, Feb. 1961, pp. 216–225.

Second-Order Elastic Deformation of Solids by Hughes et al. Physical Review, vol. 92, No. 5, Dec. 1953, pp. 1145–1149.

A Note on the Constitutive Law for Dilantance by Nur, Pageoph, vol. 113 (1975) pp. 197–206.

METHOD OF PREDICTING MECHANICAL FAILURE IN FORMATION UTILIZING STRESS DERIVATIVES WHICH MEASURE FORMATION NONLINEARITY

This application is a file wrapper continuation of parent application Ser. No. 08/298,718, filed Aug. 31, 1994, now abandoned, which is a continuation-in-part of U.S. Ser. No. 08/220,717 filed on Mar. 30, 1994, now U.S. Pat. No. 5,544,127, which is hereby incorporated by reference herein in its entirety. This application also relates to co-owned U.S. Ser. No. 08/225,016 filed Apr. 8, 1994, and now issued as U.S. Pat. No. 5,398,215, now U.S. Pat. No. 5,398,215, and co-owned U.S. Ser. No. 08/154,645 filed Nov. 19, 1993 now U.S. Pat. No. 5,485,431 which are also incorporated by reference herein in their entireties. This application further relates to co-owned U.S. Ser. Nos. 08/298,919, now U.S. Pat. No. 5,521,882 entitled Measurement of Formation Characteristics Using Acoustic Borehole Tool Having Sources of Different Frequencies" and 08/298,900, now U.S. Pat. No. 5,475,650 entitled "Measurement of Nonlinear Properties of Formation Using Sonic Borehole Tool While Changing Pressure in Borehole" which are filed on even date herewith and which are hereby incorporated by reference herein in their entireties.

BACKGROUND OF THE INVENTION

1. Field of the Invention

This invention relates broadly to methods for investigating subsurface earth formations. This invention more particularly relates to methods of utilizing determinations of acoustic nonlinear formation parameters in order to determine whether a formation is in danger of collapse.

2. State of the Art

The art of sonic well logging for use in determining formation parameters is a well established art. Sonic well logs are typically derived from sonic tools suspended in a mud-filled borehole by a cable. The tools typically include a sonic source (transmitter) and a plurality of receivers which are spaced apart by several inches or feet. Typically, a sonic signal is transmitted from the transmitter at one longitudinal end of the tool and received by the receivers at the other, and measurements are made every few inches as the tool is drawn up the borehole. Depending upon the type of transmitter or source utilized (e.g., dipole, monopole), the sonic signal generated by the transmitter travels up the borehole and/or enters the formation adjacent the borehole, and the arrival times of one or more of the compressional (P-wave), shear (S-wave), Stoneley (tube wave), and flexural wave can be detected by the receivers. The receiver responses are typically processed in order to provide a time to depth conversion capability for seismic studies as well as for providing the determinations of formations parameters such as porosity.

While measurements of the compressional and shear waves are useful in quantifying and characterizing various parameters of the formation, it will be appreciated that to date, there has been no successful mechanism for making in situ determinations of nonlinear aspects of the formation; neither has there been a mechanism for interpreting measurements of nonlinear aspects of the formation. For purposes of this invention, it should be understood that the term "nonlinear" when used to describe a material relates to the fact that a plot of stress versus strain in a material will exhibit some nonlinear behavior. In particular, the strain energy function $U(\epsilon)$ of an isotropic elastic solid can be written as:

$$U(\epsilon) = f(\lambda,\mu)\epsilon^2 + g(\alpha, \beta, \gamma)\epsilon^3 \qquad (1)$$

where $\epsilon$ is the strain, $\lambda$ and $\mu$ are the second order elastic Lamé constants, and $\alpha$, $\beta$, and $\gamma$ are the third order elastic constants. From equation (1), it will be appreciated that the stress $\sigma$ is defined by:

$$\sigma = \delta U/\delta \epsilon = f(\lambda,\mu)\epsilon + g(\alpha,\beta, \gamma)\epsilon^2 \qquad (2)$$

Based on equation (2) it is seen that the second order Lamé constants are linear constants, while the third order constants are nonlinear, and hence measure the nonlinearity of the material. The more nonlinear the stress versus strain plot is, the more nonlinear the material is said to be. Various manifestations of non-linearity include: the varying of the acoustic velocity in the material when the confining pressure changes; the varying of the acoustic velocity in the material when the amplitude of the acoustic wave changes; the interaction of two monochromatic acoustic beams having different frequencies to create third and fourth acoustic beams having the difference frequency and the additive frequency of the two incident beams; and evidence of frequencies being generated within the material which were not part of any input signal.

In the oil production industry, rock properties such as sanding, fracturing and borehole collapse can be considered to relate to the nonlinear properties of the formation. In each case, the strain in the rock catastrophically exceeds that which would be expected from a linear stress-strain relationship. As suggested in the parent and related applications hereto, since the less consolidated a formation is, the more nonlinear it is, a measurement of the nonlinearity of the formation can provide a measurement of the relative state of the consolidation of the formation. As suggested above, whether a layer of a formation is well or poorly consolidated, can broadly affect the producibility of the layer and formation, as well as the manner in which production is to be carried out.

SUMMARY OF THE INVENTION

It is therefore an object of the invention to determine through in situ measurements when a formation is nearing collapse.

It is another object of the invention to measure in situ nonlinear parameters of a formation and to relate the nonlinear parameters to formation failure.

It is a further object of the invention to provide a nonlinear formation parameter which is a direct indicator of formation collapse.

In accord with the objects of the invention, the method of the invention broadly comprises determining in situ a nonlinear parameter of a formation, and determining whether the nonlinear parameter and/or the slope of a curve of that nonlinear parameter as a function of stress has a relatively large negative value in order to determine whether the formation is subject to incipient failure. In a preferred embodiment, the nonlinear parameter of the formation is either a derivative of the square of the shear velocity with respect to formation stress, or a derivative of the square of the compressional velocity with respect to stress.

A preferred method of determining the nonlinear parameter of the formation (i.e., the derivative of the square of the shear velocity), is set forth in the previously incorporated related application Ser. No. 08/298,900, now U.S. Pat. No. 5,475,650. Briefly, velocity measurements of Stoneley and/or flexural waves, and shear and compressional waves are taken at two different pressures in the borehole, and the measurements are used in order to find values for the nonlinear parameters $N_1$ and $N_2$ which are related to the desired nonlinear parameter according to equations set forth in that related application. Alternatively, it is possible to take velocity measurements of only the shear and/or compressional waves at two different pressures in the borehole (the pressure relating to stress) and to deconvolve the effect the radial and hoop stress components on the change in velocity measurement.

According to other aspects of the invention, the slope of other indications of nonlinearity in the formation with respect to a change in stress can be used to provide an indication of incipient failure. Such indications of nonlinearity include: the amplitude of a second harmonic tube wave generated in the borehole as described in previously incorporated related application Ser. No. 08/154,645 now U.S. Pat. No. 5,485,431; the amplitude of an acoustic signal generated in the formation which has a frequency equal to the difference between two acoustic source signals as described in previously incorporated related application Ser. No. 08/298,919, now U.S. Pat. No. 5,521,882; and the variation of velocity around the circumference of the borehole as described in previously incorporated parent application Ser. No. 08/220,717 now U.S. Pat. No. 5,544,127.

Additional objects and advantages of the invention will become apparent to those skilled in the art upon reference to the detailed description taken in conjunction with the provided figures.

DETAILED DESCRIPTION OF THE PREFERRED EMBODIMENT

Figure 1:
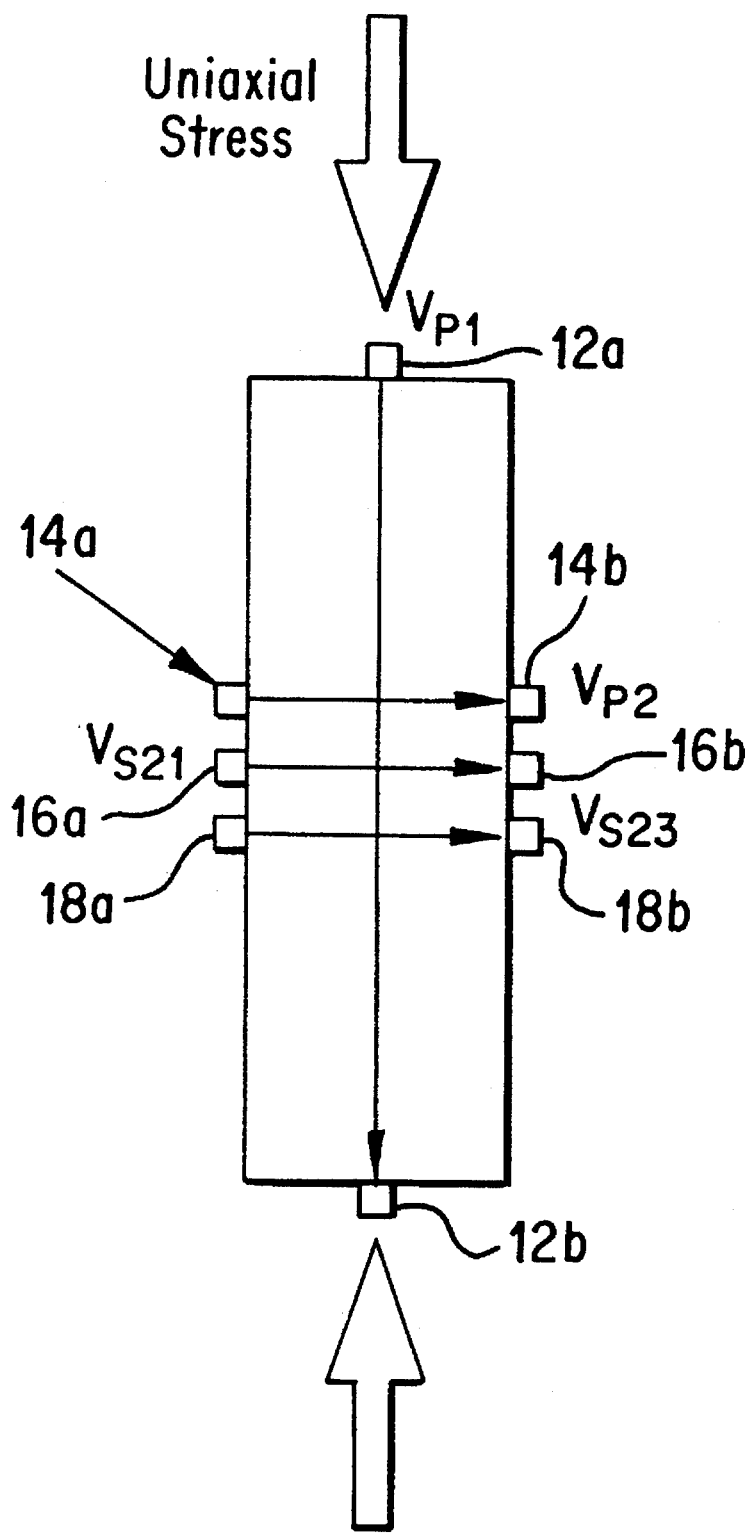
FIG. 1 is a schematic of an experimental arrangement for measuring shear and compressional velocities in a rock sample as a function of uniaxial stress.

Turning to FIG. 1, an experimental arrangement for measuring compressional and shear velocities as a function of uniaxial stress in a rock sample 21 is seen. The rock sample obtained were cylinders of approximately two inches in diameter, and six inches long. The rock samples were individually placed in a uniaxial press (not shown) which applied pressure parallel to the axis of the rock sample. Acoustic transducer pairs (sources and receivers) 12a, 12b, 14a, 14b, 16a, 16b, and 18a, 18b were mounted on each rock sample so that four different velocities could be measured:

$V_{P1}$—compressional velocity parallel to the rock axis; $V_{P2}$—compressional velocity perpendicular to the rock axis; $V_{S21}$—shear velocity perpendicular to the rock axis and polarized parallel to the rock axis; and $V_{S23}$—shear velocity perpendicular to the rock axis and polarized perpendicular to the rock axis. Three sandstones (Berea, Portland, Hanson), and one limestone (#1068) were measured. For each rock sample, uniaxial stress was increased by the press in increments until the rock eventually fractured. At each stress increment all four velocities were measured, although the velocities measured perpendicular to the applied stress ($V_{P2}$ and $V_{S23}$) were of most interest because they are believed to be most relevant to borehole failure caused by external stresses applied perpendicular to the borehole axis.

Figure 2:
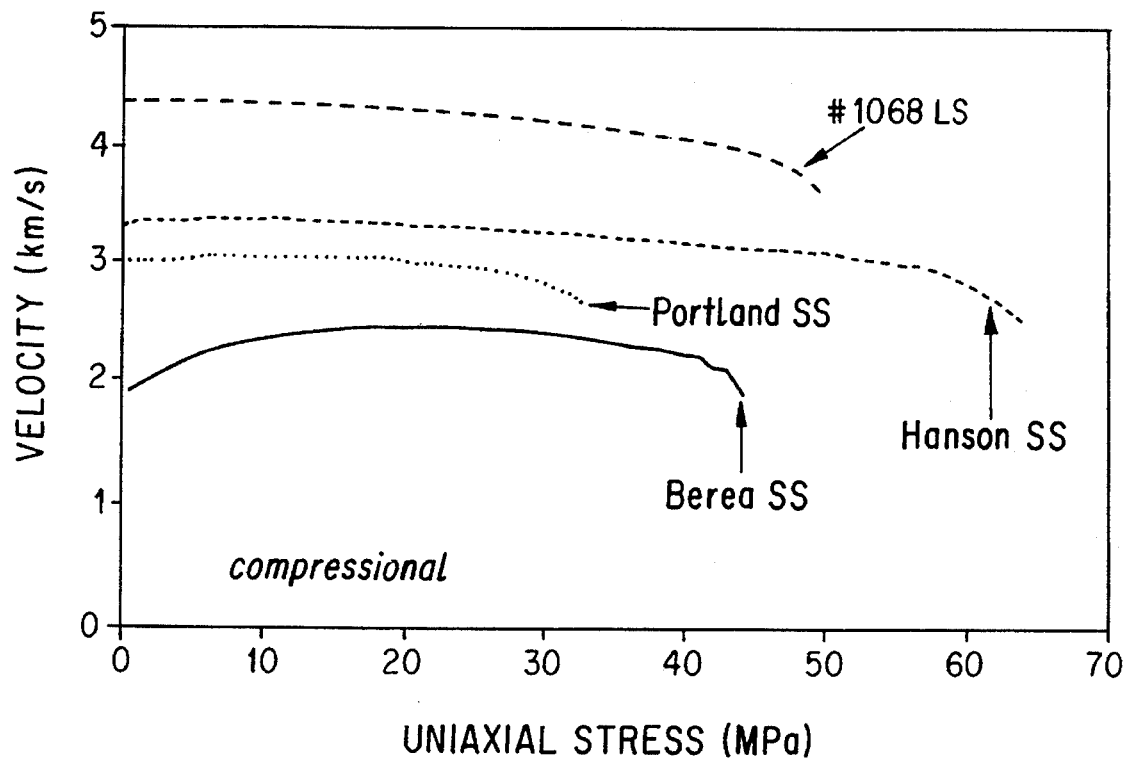
FIG. 2 is a graph of compressional velocities as a function of uniaxial stress for three rock samples.
Figure 3:
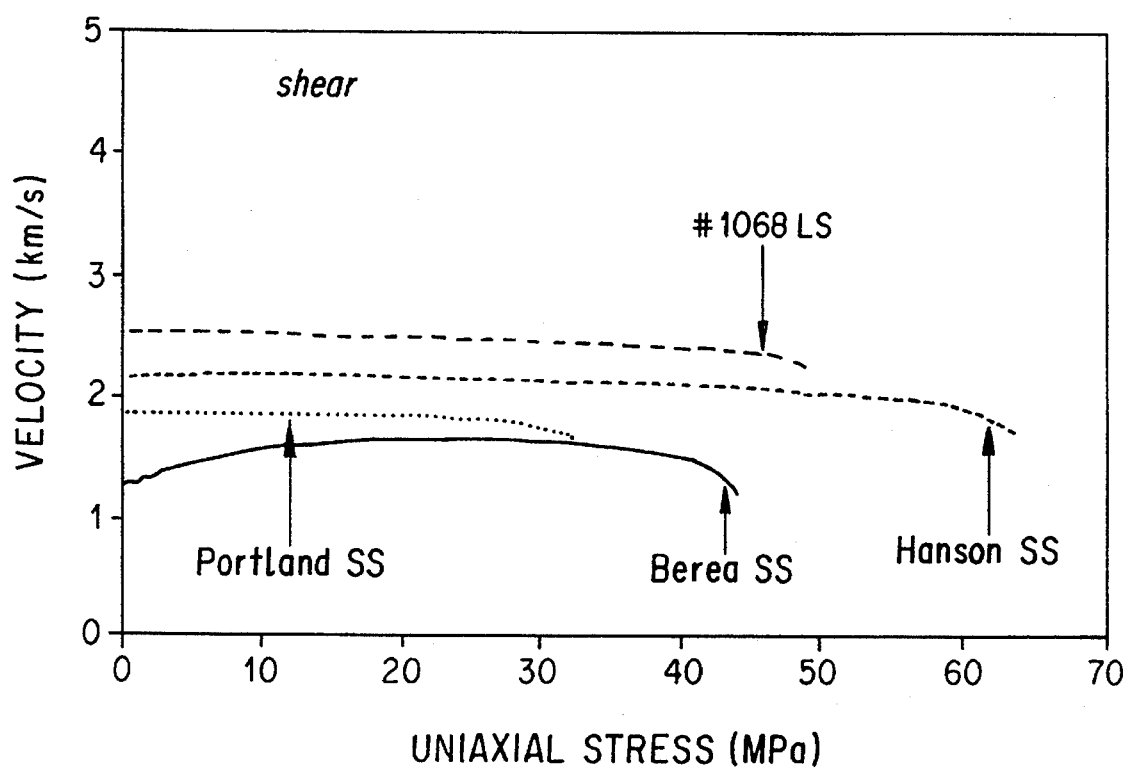
FIG. 3 is a graph of shear velocities as a function of uniaxial stress for the three rock samples.

Results of the tests on the four rock samples with respect to the perpendicularly measured velocities are seen in FIGS. 2 and 3. FIG. 2 shows compressional velocity ($V_{P2}$) versus uniaxial stress in the four samples, while FIG. 2 shows shear velocity ($V_{S23}$) versus uniaxial stress in the four samples. A review of FIGS. 2 and 3 reveals that there is no correlation between rock strength and velocity, as the higher velocity limestone sample failed before a lower velocity Hanson sandstone sample, and the Portland sandstone sample failed before the lower velocity Berea sandstone sample. What is revealed in FIGS. 2 and 3, however, is that the measured velocities decreased relatively quickly just prior to failure. This decrease is believed to result from dilatancy in the rock sample which is the opening of microcracks caused by increasing non-hydrostatic stresses. Dilatancy has previously been studied in igneous rocks in relation to earthquake prediction, and was also observed in unconsolidated sand. See Nur, A. "A Note on the Constitutive Law for Dilatancy", *Pageoph*, Vol. 113 (1975).

As set forth in the related cases hereto, the variation in the square of the shear or compressional velocities as a function of stress is a fundamental indication of formation nonlinearity. This may also be derived from an equation for compressional velocity in a hydrostatically stressed isotropic medium set forth by Hughes, D. S. and Kelly, J. L. "Second-Order Elastic Deformation of Solids", *Physical Review* 92,5; p.1145 (1953):

$$\rho_0 V_P^2 \lambda + 2\mu - (P/3K)[6l + 4m + 7 + 10\mu] \qquad (3)$$

where $\rho_0$ is the mass density of the formation, $V_P$ is the compressional wave velocity, P is the applied pressure, $\lambda$ and $\mu$ are the Lamé constants, and l and m are third order (nonlinear) elastic constants. From equation (3), it can be seen that the compressional velocity squared, as a function of stress (via hydrostatic pressure P) is directly proportional to the nonlinear constants l and m (and the linear Lame constants). Based on equation (3), and recognizing that the nonlinear coefficients l and m are typically at least two orders of magnitude greater than the linear coefficients, it will be appreciated that if the velocity does not significantly vary with stress, the rock is considered to be linear. However, if the velocity does significantly vary with stress, the rock can be described as having nonlinear characteristics. Thus, the derivative of the square of the velocity as a function of stress may be considered a direct indication of formation nonlinearity.

Figure 4:
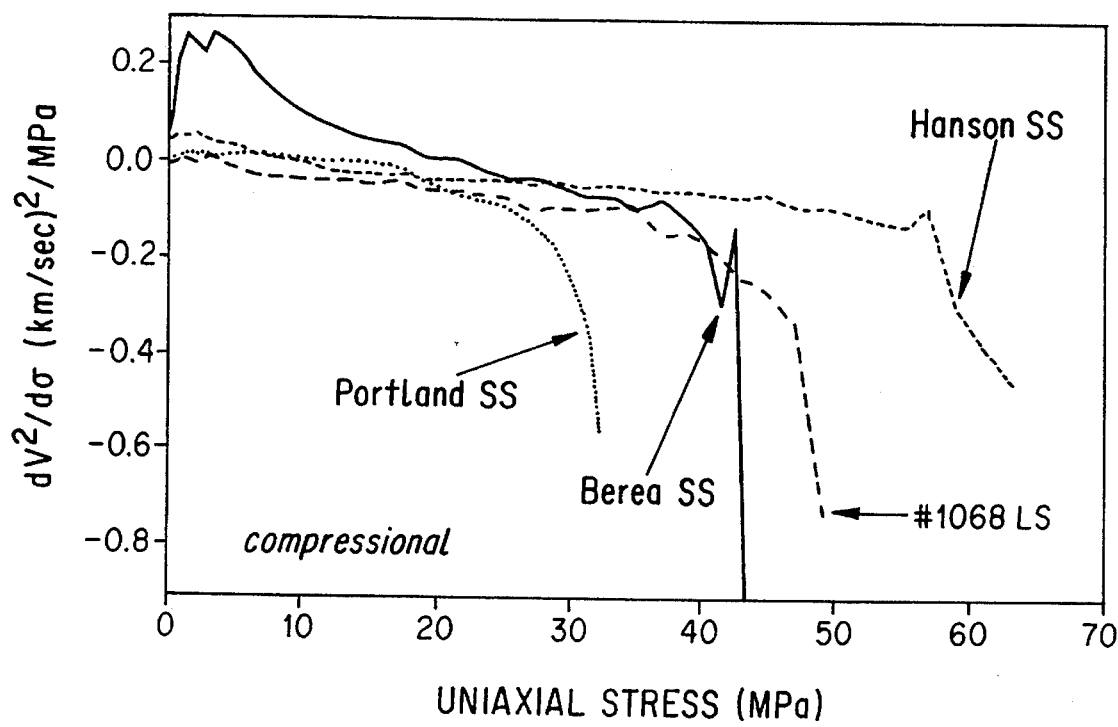
FIG. 4 is a graph of the nonlinear parameter $dV^2/d\sigma$ as a function of uniaxial stress for compressional waves measured in the three rock samples and a fourth rock sample.
Figure 5:
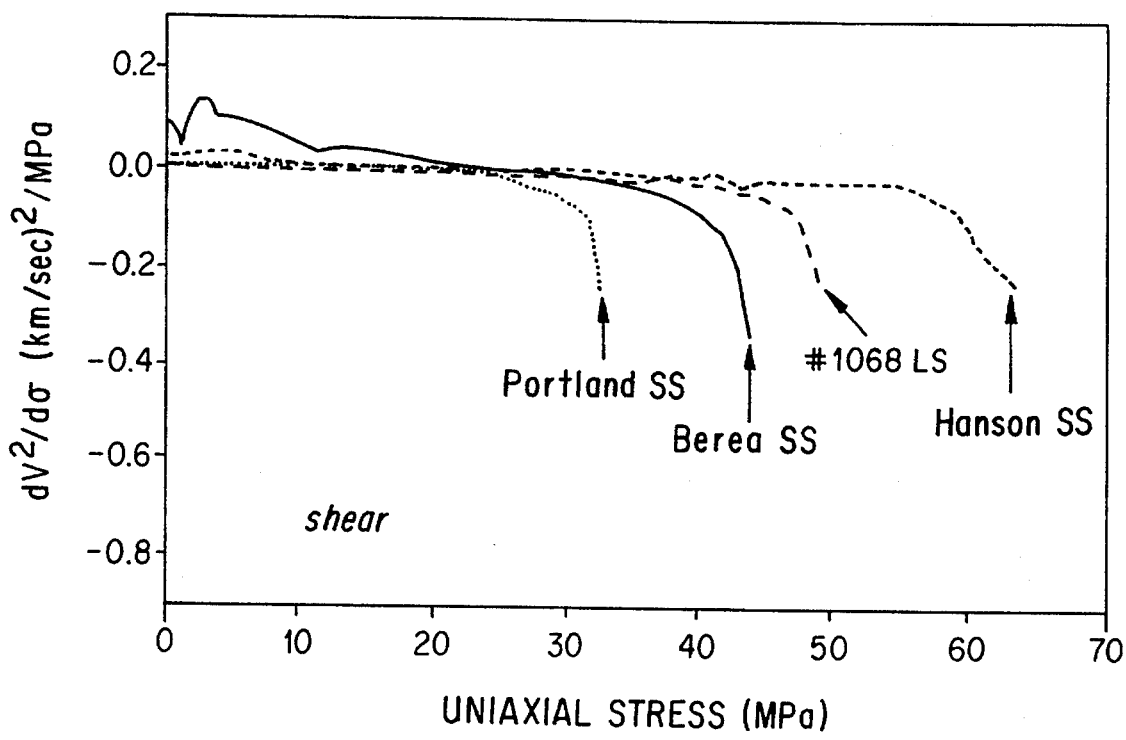
FIG. 5 is a graph of the nonlinear parameter $dV^2/d\sigma$ as a function of uniaxial stress for shear waves measured in the four rock samples.

Using the data obtained with reference to FIGS. 2 and 3, values were derived and plotted of the derivative with respect to stress of the square of the velocity ($dV^2/d\sigma$) as a function of stress as seen in FIGS. 4 and 5. FIG. 4 relates to the derivatives of the perpendicular compressional wave velocities, while FIG. 5 relates to the derivatives of the shear wave velocities. As seen in FIGS. 4 and 5, the values of the derivatives drop significantly just prior to rock failure. In fact, it can be seen that a compressional derivative value of between approximately −0.15 and −0.4 (km/sec)$^2$/MPa, with a preferred value of −0.2 (km/sec)$^2$/MPa can be taken as a defining value of incipient failure as all the rock samples failed within about 10 MPa to 1 MPa after the compressional derivative value dropped below that value range. Likewise, a shear derivative value of approximately −0.075 to −0.2 (km/sec)$^2$/MPa, with a preferred value of −0.1 (km/sec)$^2$/MPa was likewise a defining indication of incipient failure as all the rock samples failed within about 5 to 0.5 MPa after the shear derivative value dropped below that value range. It should be appreciated that the defining indications of incipient failure relate to the experimental arrangement of FIG. 1 where there was no overburden pressure. Thus, it is possible that in the formation different values for defining indications of incipient failure will be obtained.

It will also be appreciated that the slope of the derivative curves can be used as an indication of incipient failure as the slopes become large (negative) just prior to rock failure. A preferred negative slope value range defining an indication of incipient failure is between −0.02 to −0.07 (km/sec)$^2$/(MPa)$^2$, with a preferred value of −0.06 (km/sec)$^2$/MPa$^2$ as rocks will typically fail if uniaxially stressed between 5—1 MPa beyond that point. Again it is noted that these values relate to the experimental arrangement of FIG. 1, and that it is possible that via experimentation in the borehole, other values might be found in formations with overburden pressures.

Figure 6:
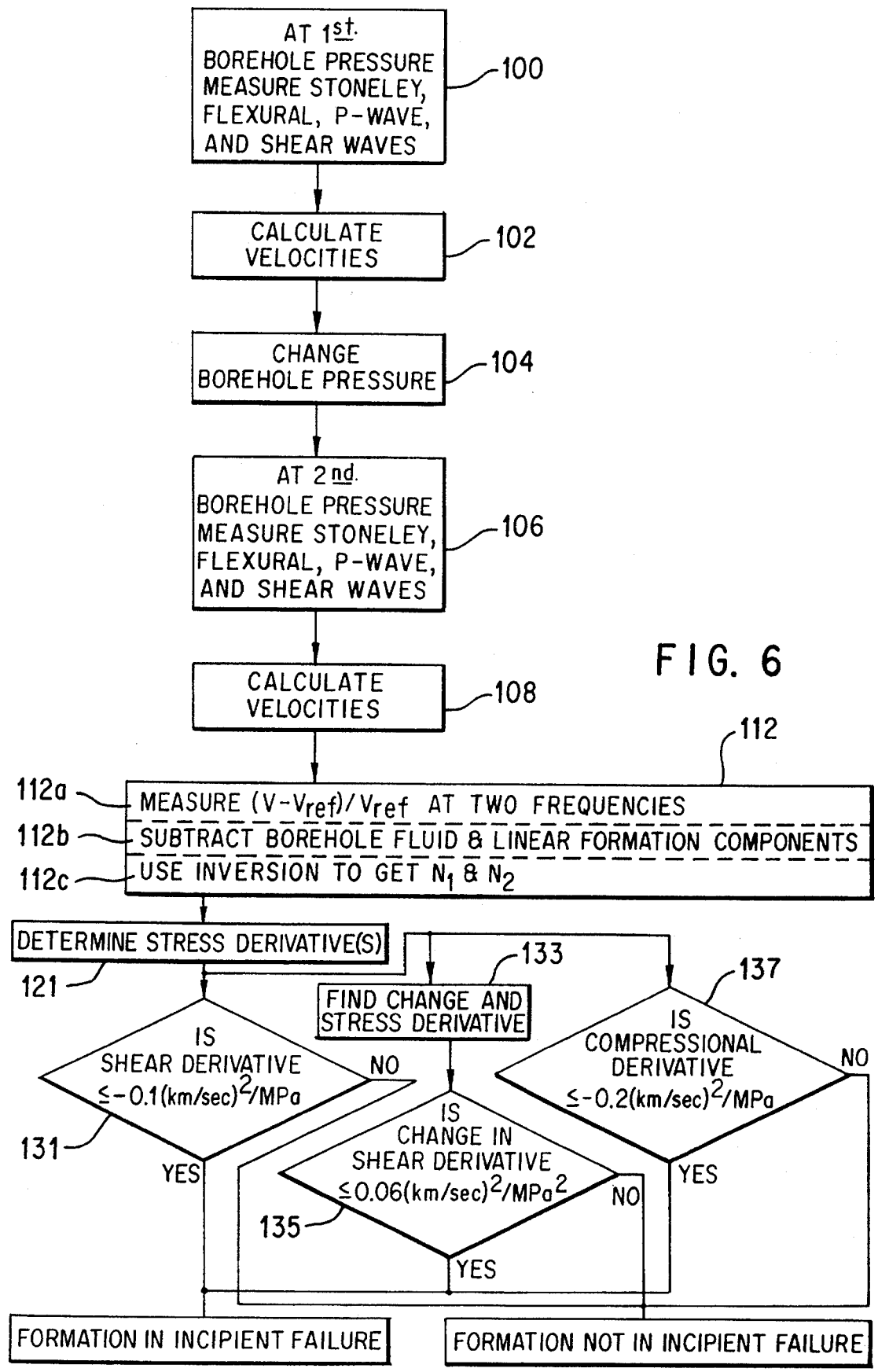
FIG. 6 is a flow diagram of a preferred method of obtaining in situ a determination of the nonlinear parameter $dV^2/d\sigma$.

A preferred manner of determining the derivative of the shear velocity squared with respect to stress ($dV_x^2/d\sigma$) is set forth in previously incorporated related patent application Ser. No. 08/298,900, now U.S. Pat. No. 5,475,650. However, for purposes of completeness, a brief review is included herein. Thus, as seen in FIG. 6, using a borehole tool having a monopole and/or dipole source and acoustic detectors, at 100 the velocity of Stoneley and/or flexural waves, and compressional and shear waves generated by the source(s) are measured. The velocities (including velocity dispersion curves for the Stoneley and flexural waves) are calculated at step 102 by a processor which is either connected to the acoustic detectors in the borehole tool, or is located uphole and coupled to the borehole tool via a wireline. At 104, the borehole pressure at the location of the borehole tool is changed, either by providing the borehole tool with packers which seal off that area of the borehole and a fluid injection means for increasing the pressure in the borehole, or by locating a packer type device on a well head in order to pressurize the entire borehole. Then at 106, at the second pressure, Stoneley and/or flexural waves, and compressional and shear waves are generated and measured again, and at 108, wave velocities at the second pressure are calculated. Using the change in Stoneley and/or flexural wave velocities, as well as the p-wave and s-wave velocities, values for the nonlinear formation parameters $N_1$ and $N_2$ are found at step 112. In particular, for each of at least two frequencies (at least one of which is preferably in the 3 kHz to 6 kHz range), a fractional change in the measured acoustic velocity is made at step 112a. From the fractional change, a component generated by the borehole fluid and a component due to linear aspects of the formation are subtracted at step 112b to provide a frequency dependent nonlinear formation component (B). Then, utilizing an inversion process AX=B at step 112c according to the following equations (4)–(7), values are obtained for the nonlinear parameters $N_1$ and $N_2$:

$$A = |C_1^{f_1} \ C_2^{f_1}| \ |C_1^{f_2} \ C_2^{f_2}| \tag{4}$$

$$X = |N_1 \Delta P| \ |N_2 \Delta P| \tag{5}$$

$$B = |(\Delta v/v|_{Stoneley} - \Delta v/v|_{linear} - \Delta v/v|_{fluid})_{f1}| \ |(\Delta v/v|_{Stoneley} - \Delta v/v|_{linear} - \Delta v/v|_{fluid})_{f2}| \tag{6}$$

where $$\Delta v/v \ |_{Stoneley} = (v^{Stoneley} - v_{ref}^{Stoneley})/v_{ref}^{Stoneley} \tag{7}$$

and where $v_{ref}^{Stoneley}$ is the velocity of the Stoneley (or flexural) wave in an unpressurized borehole (or in a borehole at a given reference pressure), $v^{Stoneley}$ is the measured velocity of the dispersive Stoneley (or flexural) wave at a known pressure, $\Delta P$ is the difference in pressure between the reference pressure and the known pressure, $\Delta v/v|_{linear}$ is the portion of the fractional change in the Stoneley (or flexural) dispersion caused by an increase in the borehole pressure that can be calculated from the linear constants of the formation in the ambient state, $\Delta v/v|_{fluid}$ is the portion of the fractional change in the Stoneley (or flexural) dispersion caused by an increase in the borehole pressure that can be calculated from the known borehole fluid nonlinearity in the ambient state, and $C_1$ and $C_2$ are volume integrals which are a function of frequency and are calculable in terms of the Stoneley (or flexural) wave solution in the ambient state. Additional details may be found in related patent application Ser. No. 08/298,900, now U.S. Pat. No. 5,475,650 regarding the volume integrals, as well as the fractional changes in the Stoneley or flexural dispersions caused the increase in the borehole pressure due to the linear constants of the formation and due to the borehole fluid nonlinearity.

With values determined for nonlinear parameters $N_1$ and $N_2$, a determination of a value for the shear derivative $dV_s^2/d\sigma$ can be made. In particular, as set forth in the related patent application Ser. No. 08/298,900, where a specimen is in the form of a rod with uniaxial stress applied along the rod axis (i.e., stresses normal to the rod axis are assumed to be zero), a stress derivative of the shear waves propagating normal to the rod axis and polarized normal to the stress direction can be approximated by:

$$\frac{\partial V_{S23}^2}{\partial S} = \frac{(vN_2 - N_1)c_{66}}{p_0 Y} + \frac{(N_2 - 2)vc_{66}}{p_0 Y}, \tag{8}$$

where $N_1 = -c_{144}/c_{66}$ and $N_2 = -c_{155}/c_{66}$, and $\lambda$ and Y are respectively Poisson's ratio and Young's modulus in the formation in the reference ambient state. The Poisson's ratio and Young's modulus are a function of the second order constants of the formation and can be expressed by:

$$v = \frac{c_{12}}{2(c_{12} + c_{66})}, \tag{9}$$

$$Y = \frac{c_{66}(3c_{12} + 2c_{66})}{(c_{12} + c_{66})} \tag{10}$$

On the other hand, if the specimen is long along the propagation direction, a plane strain approximation normal to the propagation direction is an appropriate assumption. In this case, the stress derivative of the shear wave polarized normal to the stress direction is given by:

$$\frac{\partial V_{S23}^2}{\partial S} = N_1 \frac{(v^2 - 1)c_{66}}{p_0 Y} - (2 - N_2) \frac{v(1 + v)c_{66}}{p_0 Y}. \tag{11}$$

Therefore, the stress derivative of $V_{S23}^2$ can be readily approximated from either equations (8) or (11), and typically, the stress derivatives for a rock sample will fall between these approximations. Thus, at 121 of FIG. 6, the stress derivative of $V_{S23}^2$ (i.e., $dV_{S23}^2/d\sigma$) is calculated according to equations (8) and/or (11). If the stress derivative is calculated in accordance with both sets of equations, the results may be averaged if desired.

As set forth above, once a value for the stress derivative is calculated, a determination can be made as to whether the formation is in danger of incipient failure. For example, as suggested at 131 of FIG. 6, the determined value of the shear derivative can be compared to a desired threshold value such as $-0.1$ (km/sec)$^2$/MPa. If the shear derivative is less than or equal to the desired threshold value, incipient formation failure can be declared; whereas, if the shear derivative is greater than the threshold value, the formation can be declared to be not near failure. Alternatively, or in addition, at 133, the change in the stress derivative as a function of stress can be obtained at the ambient state, and at 135, this value can be compared to another desired threshold value such as $-0.06$ (km/sec)$^2$/MPa$^2$. If the value of the change in the stress derivative as a function of stress is less than or equal to that threshold value, incipient formation failure can be declared, whereas, if the derivative of the shear derivative is greater than that threshold value, the formation can be declared to be not near failure. Further yet, if a value for the compressional derivative is obtained, that value can be compared at 137 to yet another desired threshold value such as $-0.2$ (km/sec)$^2$/MPa. Again, if the compressional derivative is less than or equal to the compressional derivative threshold value, incipient formation failure can be declared, whereas if the compressional derivative is greater than the threshold value, the formation can be declared to be not near failure. Likewise, if a derivative with respect to stress of the compressional derivative is obtained, that value can be compared to the same threshold value as the derivative of the shear derivative to determine incipient formation failure.

It will be appreciated that, if desired, other threshold values can be utilized. For example, the threshold shear derivative value is preferably chosen between approximately $-0.075$ to $-0.2$ (km/sec)$^2$/MPa, while the threshold derivative of the shear (or compressional) derivative value is preferably chosen between $-0.02$ to $-0.07$ (km/sec)$^2$/(MPa)$^2$. The threshold compressional derivative value is preferably chosen between approximately $-0.15$ and $-0.4$ (km/sec)$^2$/MPa. However, yet other threshold values can be utilized.

An alternative manner of determining the in situ value of $dV^2/d\sigma$ is to take velocity measurements of only the shear and/or compressional waves at two different pressures in the borehole (the pressure relating to stress) and to deconvolve the effect the radial and hoop stress components on the change in velocity measurement.

According to other aspects of the invention, the slope of other indications of nonlinearity in the formation with respect to a change in stress (i.e., the derivative with respect to stress) can be used to provide an indication of incipient failure. Such indications of nonlinearity include: the amplitude of a second harmonic tube wave generated in the borehole as described in previously incorporated related application Ser. No. 08/154,645; the amplitude of an acoustic signal generated in the formation which has a frequency equal to the difference between two acoustic source signals as described in previously incorporated related application Ser. No. 08/298,919 (Docket #SDR-033) now U.S. Pat. No. 5,521,882; and the variation of velocity around the circumference of the borehole as described in previously incorporated parent application Ser. No. 08/220,717 now U.S. Pat. No. 5,544,127.

There have been described and illustrated herein methods for predicting mechanical failure in formations. While particular embodiments have been described, it is not intended that the invention be limited thereto, as it is intended that the invention be as broad in scope as the art will allow and that the specification be read likewise. Thus, while particular preferred stress and compressional derivative threshold values and ranges were provided for determining whether a formation is in incipient failure, it will be appreciated that other thresholds could be utilized. Also, while preferred methods of obtaining in situ values for the derivative with respect to stress of the square of the shear velocity ($dV_s^2/d\sigma$) were described, it will be appreciated that other methods could be utilized within the scope of the invention. It will therefore be appreciated by those skilled in the art that yet other modifications could be made to the provided invention without deviating from its spirit and scope as so claimed.

I claim:

1. A method for determining in situ incipient stress failure of an underground formation traversed by a borehole, comprising:

(a) positioning a tool having an acoustic source and at least one receiver in the borehole near the formation;

(b) transmitting an acoustic signal from the source into the formation and detecting the signal with the at least one receiver after it has propagated through the formation;

(c) determining, from the received signal, at least one of a compressional wave velocity and a shear wave velocity;

(d) determining, from at least one of the compressional wave velocity and the shear wave velocity, a value of a non-linear parameter of the formation; and (e) comparing the value of the non-linear parameter with a threshold value so as to determine incipient stress failure of the formation.

2. A method as claimed in claim 1, wherein the non-linear parameter is a derivative of squared shear velocity with respect to formation stress.

3. A method as claimed in claim 2, wherein the threshold value is chosen from the range $-0.075$ (km/sec)$^2$/MPa to $-0.2$ (km/sec)$^2$/MPa.

4. A method as claimed in claim 3, wherein the threshold value is about $-0.1$ (km/sec)$^2$/MPa.

5. A method as claimed in claim 1, wherein the non-linear parameter is a derivative of squared compressional velocity with respect to formation stress.

6. A method as claimed in claim 5, wherein the threshold value is chosen from the range $-0.15$ (km/sec)$^2$/MPa to $-0.4$ (km/sec)$^2$/MPa.

7. A method as claimed in claim 6, wherein the threshold value is about $-0.2$ (km/sec)$^2$/MPa.

8. A method as claimed in claim 5, wherein the parameter is a non-linear parameter comprising at least one of a derivative of squared shear velocity with respect to formation stress, and a derivative of squared compressional velocity with respect to formation stress, and a derivative of squared compressional velocity with respect to formation stress.

9. A method as claimed in claim 8, wherein the threshold value is chosen from the range $-0.02$ (km/sec)$^2$/MPa to $-0.07$ (km/sec.)$^2$/MPa.

10. A method as claimed in claim 9, wherein the threshold value is about $-0.06$ (km/sec)$^2$/(MPa)$^2$.

11. A method for determining in situ incipient stress failure of an underground formation traversed by a borehole, comprising:

(a) positioning a tool having an acoustic source and at least one receiver in the borehole near the formation;

(b) transmitting an acoustic signal from the source into the formation and detecting the signal with the at least one receiver after it has propagated through the formation;

(c) determining, from the received signal, at least one of a compressional wave velocity and a shear wave velocity;

(d) determining, from at least one of the compressional wave velocity and the shear wave velocity, a value of a parameter indicative of non-linearity of a relationship between formation strain as defined by a strain energy function $U(\epsilon)=f(\lambda/\mu)\epsilon^2+g(\alpha, \beta,\gamma)\epsilon^3$, wherein e is the strain, l and m are second order elastic Lame constants, and formation stress as defined by $\sigma=\delta U/\delta\epsilon=f(\lambda, \mu)\epsilon+g(\alpha, \beta, \gamma)\epsilon^2$; and (e) comparing the value of the parameter indicative of non-linearity with a threshold value so as to determine incipient stress failure of the formation.

12. A method as claimed in claim 11, further comprising determining at least one of sanding, fracturing and borehole collapse.

13. A method as claimed in claim 11, further comprising determining a degree of relative consolidation of the formation.

14. A method as claimed in claim 11, further comprising determining a parameter related to the producibility of fluids from the formation into the borehole.

15. A method as claimed in claim 11, further comprising using the value to and the comparison to determine a manner in which fluids are produced from the formation.

16. A method as claimed in claim 1, wherein the steps of transmitting and receiving the acoustic signal are repeated at two different pressures in the borehole so as to determine values of the parameter at these pressures.

17. A method as claimed in claim 11, further comprising determining at least one of Stoneley velocity and flexural velocity.

* * * * *